United States Patent
Gammon

(10) Patent No.: US 6,719,735 B1
(45) Date of Patent: Apr. 13, 2004

(54) SYRINGE ADAPTER

(75) Inventor: James H. Gammon, Manasquan, NJ (US)

(73) Assignee: Gammon Technical Products, Inc., Manasquan, NJ (US)

( * ) Notice: Subject to any disclaimer, the term of this patent is extended or adjusted under 35 U.S.C. 154(b) by 0 days.

(21) Appl. No.: 10/377,216

(22) Filed: Feb. 28, 2003

(51) Int. Cl.[7] .............................................. A61M 5/315
(52) U.S. Cl. ...................................... 604/220; 604/218
(58) Field of Search ................................ 604/220, 218, 604/221, 223, 227, 228, 233, 235, 187

(56) References Cited

U.S. PATENT DOCUMENTS

| | | | |
|---|---|---|---|
| 3,990,446 A | * 11/1976 | Taylor | .......................... 604/210 |
| 4,846,801 A |   7/1989 | Okuda et al. | |
| 4,997,423 A |   3/1991 | Okuda et al. | |
| 5,135,511 A | * 8/1992 | Houghton et al. | .......... 604/220 |
| 5,241,969 A |   9/1993 | Carson et al. | |
| 5,242,405 A |   9/1993 | Howe | |
| 5,458,576 A | 10/1995 | Haber et al. | |
| 5,469,860 A | * 11/1995 | De Santis | .................... 600/578 |
| 5,512,054 A |   4/1996 | Morningstar | |
| 5,554,132 A |   9/1996 | Straits et al. | |
| 5,582,595 A | * 12/1996 | Haber et al. | ................. 604/187 |
| 5,807,340 A | * 9/1998 | Pokras | ........................ 604/183 |
| 5,830,152 A | * 11/1998 | Tao | ............................ 600/562 |

* cited by examiner

Primary Examiner—Manuel Mendez
(74) Attorney, Agent, or Firm—MacMillan, Sobanski & Todd; Donald R. Fraser

(57) ABSTRACT

A syringe and adapter combination allowing the syringe to be filled with fluid by the employment of one hand of an operator.

2 Claims, 3 Drawing Sheets

SYRINGE ADAPTER

BACKGROUND OF THE INVENTION

1. Field of the Invention

The present invention relates to a hand grip adapter for use with a syringe and, more particularly, to a hand grip adapter and a syringe combination which results in the use of the syringe with one hand of an operator.

2. Description of the Prior Art

Typically, the action of injection of a syringe involves closing the hand of the operator, wherein the thumb is under compression against the plunger, the direction of normal strength of the thumb. Syringes, as used in the medical industry and other industries, are easy to operate on the injection stroke, but much more difficult to draw as a suction stroke. When used for injection, the thumb pushes the plunger down and the fingers hold the body of the syringe steady. The problem is in the reverse operation of a syringe, used to draw liquid into the syringe. The task usually requires two hands.

It is an object of this invention to produce a hand grip for a syringe which can be operated in the suction stroke with the thumb under compression, allowing the operation to be accomplished with one hand.

Another object of the invention is to produce a hand grip for a syringe which will facilitate efficient preparation of samples of fluid to be tested.

SUMMARY OF THE INVENTION

The above, as well as other objects, may typically be achieved by a hand grip adapter for use with an associated syringe having a hollow cylindrical body having an outlet at one end and a laterally extending flange at the opposite end, a piston disposed within and adapted for reciprocal movement in the body, a shaft attached to the piston and extending outwardly of the body at the opposite end and operative to impart reciprocal movement to the piston, and finger gripping means extending from the shaft, the adapter comprising a thumb compression member, means engageable with the flange of the cylindrical body of the syringe, and arm means interconnecting the thumb compression member and the means engageable with the flange of the associated syringe to maintain a fixed spaced relation therebetween whereby when the thumb compression member and the finger gripping means of the syringe are caused to be manually moved toward one another, causing relative reciprocal movement between the body of the syringe and the piston forcing the piston to be moved away from the outlet.

BRIEF DESCRIPTION OF THE DRAWINGS

The above objects and advantages of the invention will become readily apparent to those skilled in the art from reading the following detailed description of the invention when considered in the light of the accompanying drawings, in which.

DETAILED DESCRIPTION OF THE PREFERRED EMBODIMENT

Figure 1:
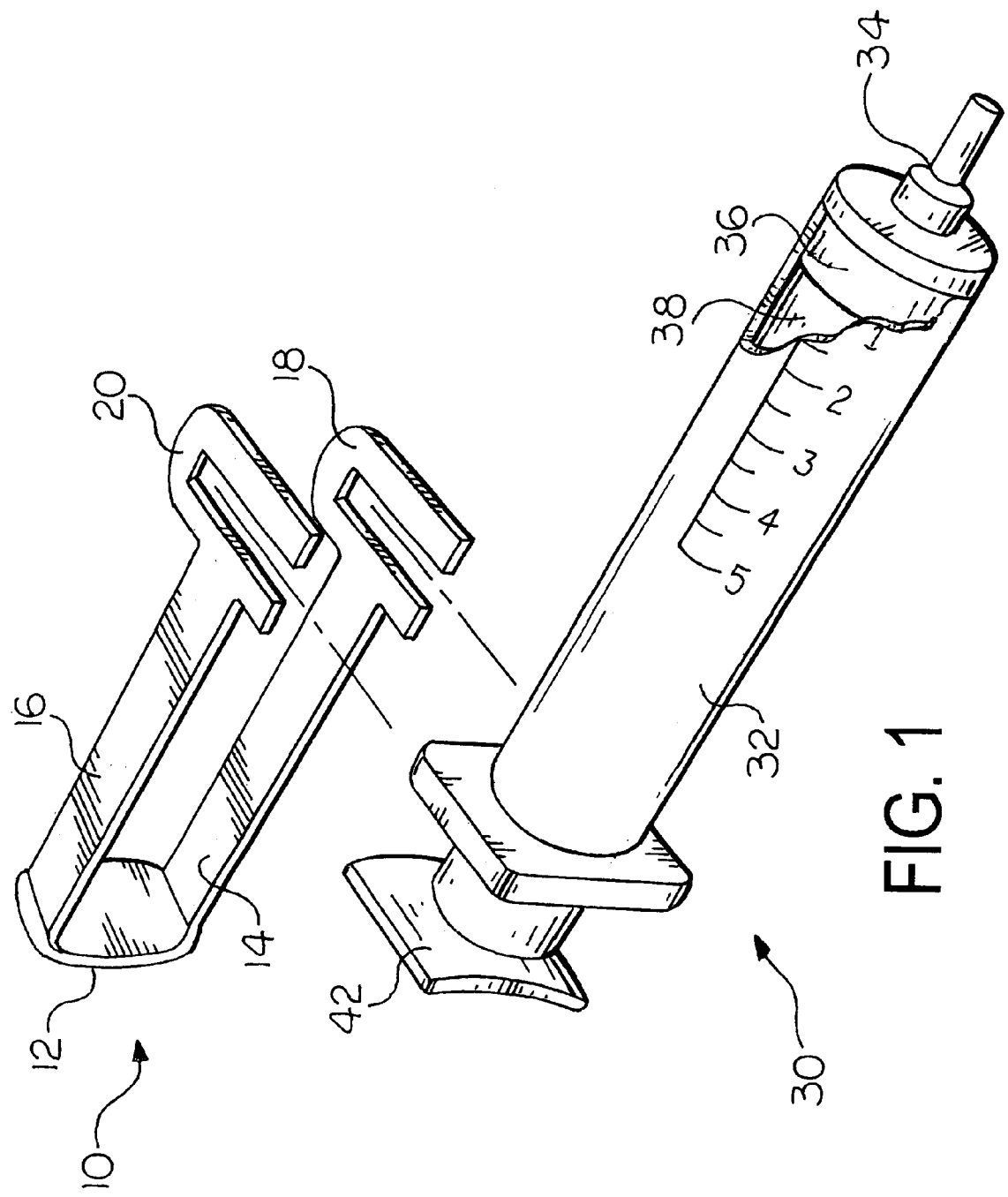
FIG. 1 is a perspective exploded view of a syringe and an adapter embodying the features of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiments illustrated.

With reference first to FIG. 1, therein is illustrated a hand grip adapter device 10 embodying the present invention. As will be further described, the present hand grip releasably secures a syringe plunger shaft so that the user can fill the syringe with the operation of a thumb and two-finger grip.

With particular reference to FIG. 1, the hand grip adapter device 10 includes a thumb pad 12 and a pair of spaced apart legs 14, 16 depending therefrom. The terminal ends of the legs 14, 16 are provided with generally C-shaped brackets 18, 20, respectively. The device 10 can be formed of any suitable rather rigid material such as metal or plastic.

The device 10 is designed to be used with a syringe 30 of the type generally illustrated which includes a hollow cylindrical body 32 having a narrowed outlet 34 at one end for drawing in or ejecting fluid by an internal piston 36 and an associated shaft 38 connected at one end thereof for effecting reciprocal movement of the piston 36. A laterally extending flange member 40 is integral with the cylindrical body 32 at the end opposite the outlet 34.

The piston shaft 38 extends outwardly of the cylindrical body 32. A finger grasping extension 42 is attached to the terminal end of the shaft 38. Generally, the syringe 30 is filled with a fluid by causing the cylindrical body 32 to be held tightly by one hand and moving the piston 36 away from the outlet 34 by pulling the finger grasping extension 42 with the other hand.

The present invention enables the filling of the syringe 30 with the use of only one hand of the operator.

In use, reference should be made to all of the drawings. Initially, the adapter device 10 is positioned such that the open ends of the C-shaped brackets 18, 20 are aligned with and then caused to receive opposite portions of the flange 40 as. illustrated in FIGS. 2 and 3.

Figure 2:
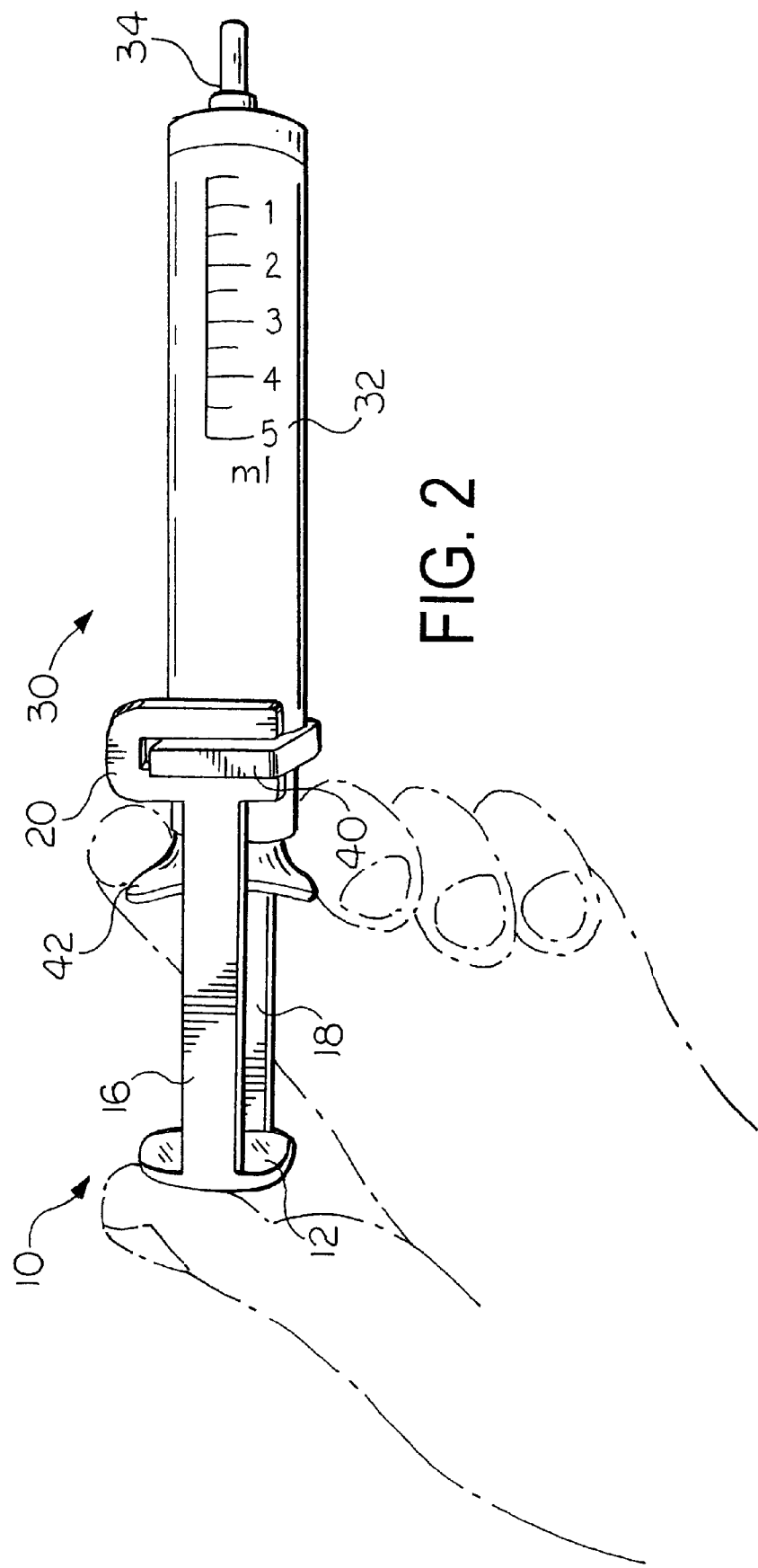
FIG. 2 is a view of the syringe and the adapter mounted thereon.
Figure 3:
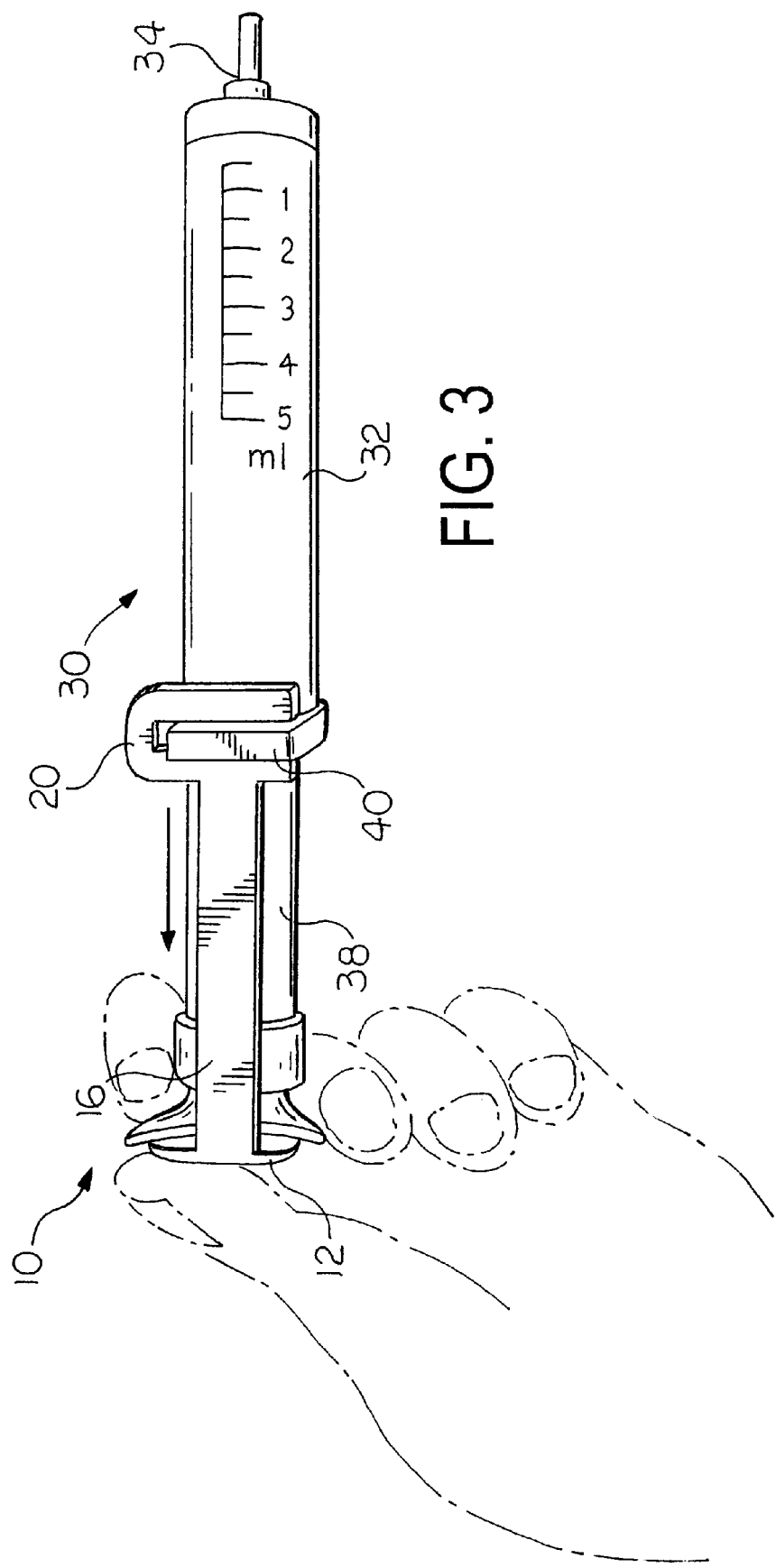
FIG. 3 is a view of the syringe and adapter illustrated in FIG. 2 showing the piston of the syringe moved to a filled position.

The user then grasps the assemblage by placing the thumb of the left hand, as illustrated in FIG. 2, on the thumb pad 12 and positioning the finger grasping extension 42 between the index finger and the middle finger on the undersurface of the extension 42. Then, the thumb is pressed against the thumb pad 12 and the index finger and the middle finger of the user squeeze the under-surface of the extension 42 causing the shaft 38 to move the piston 36 away from the outlet 34. Thus, the reciprocal movement of the piston 36 within the interior of the cylindrical body 32 creates a suction of the outlet 34 tending to draw fluid in which the outlet 34 is immersed into the hollow interior of the body 32.

In the event the cylindrical body 32 is formed of transparent or translucent material, the quantity of fluid drawn into the hollow body 32 may be closely metered by sight alone or with the use of volumetric indicia printed thereon.

It will further be appreciated that width of the legs 14 and 16 and the extension 42 must be such as to permit placement of the operator's index finger and third finger readily on the undersurface of the extension to enable proper operation of the assemblage.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A hand grip adapter for use with an associated syringe having a hollow cylindrical body having an outlet at one end and a laterally extending flange at the opposite end, a piston disposed within and adapted for reciprocal movement in the body, a shaft attached to the piston and extending outwardly of the body at the opposite end and operative to impart reciprocal movement to the piston, and finger gripping means extending from the shaft, the adapter comprising:

a thumb compression member;

a pair of legs, each of said legs having a distal end and a proximal end, the proximal ends of said legs secured to said thumb compression member to cause said legs to depend from said thumb compression member in fixed spaced relation to one another and terminating in the distal ends; and brackets secured to the distal ends of said legs, said brackets spaced from one another and having parallel slots adapted to slidingly receive the flange of the cylindrical body of the syringe, whereby when said thumb compression member and the finger gripping means of the syringe are caused to be manually moved toward one another, relative reciprocal movement is imparted between the body of the syringe and the piston, thereby forcing the piston to be moved away from the outlet of the syringe.

2. A syringe comprising:

a hollow cylindrical body having an outlet at one end and an outwardly extending flange at the opposite end;

a piston within said body;

a shaft for imparting reciprocal movement to said piston having one end connected to said piston and other end extending out of the opposite end of said body;

finger gripping means affixed to the other end of said piston;

a thumb compression member;

a pair of legs, each of said legs having a distal end and a proximal end, the proximal ends of said legs secured to said thumb compression member to cause said legs to depend from said thumb compression member in fixed spaced relation to one another and terminating in the distal ends; and brackets secured to the distal ends of said legs, said brackets spaced from one another and having parallel slots adapted to slidingly receive the flange of the cylindrical body of the syringe, whereby when the distance between said thumb compression member and said finger gripping means is varied, a similar variance occurs with said piston.

* * * * *